United States Patent [19]

Feuer

[11] 4,001,396
[45] Jan. 4, 1977

[54] HORMONAL PRODUCT EXTRACTED FROM PARATHYROID GLAND AND PROCESS FOR THE PREPARATION THEREOF

[75] Inventor: Laszlo Feuer, Budapest, Hungary

[73] Assignee: Chinoin Pharmaceutical and Chemical Works Ltd., Budapest, Hungary

[22] Filed: Apr. 3, 1974

[21] Appl. No.: 457,627

Related U.S. Application Data

[63] Continuation-in-part of Ser. No. 274,723, July 24, 1972, abandoned.

[30] Foreign Application Priority Data

Aug. 4, 1971 Hungary .............................. CI 1146

[52] U.S. Cl. ................................................ 424/112
[51] Int. Cl.² ...................................... A61K 35/46
[58] Field of Search .................................... 424/112

[56] References Cited

UNITED STATES PATENTS

| | | | |
|---|---|---|---|
| 1,865,164 | 6/1932 | Berman | 424/112 |
| 1,890,851 | 12/1932 | Hanson | 424/112 |
| 1,984,260 | 12/1934 | Evers et al. | 424/112 |

OTHER PUBLICATIONS

Pincus et al., The Hormones, vol. III, (1955) pp. 164–168.

*Primary Examiner*—Sam Rosen
*Attorney, Agent, or Firm*—Karl F. Ross; Herbert Dubno

[57] ABSTRACT

A deproteinized, defatted aqueous extract of the parathyroid gland insoluble in benzene, chloroform and carbontetrachloride. The composition has vitamin-A type activity and is generally effective for the treatment of irradiation injury.

4 Claims, No Drawings

HORMONAL PRODUCT EXTRACTED FROM PARATHYROID GLAND AND PROCESS FOR THE
PREPARATION THEREOF

CROSS-REFERENCE TO RELATED APPLICATION

The present application is a continuation-in-part of the copending application Ser. No. 274,723 filed 24 July 1972, now abandoned.

FIELD OF THE INVENTION

My present invention related to a hormonal substance derived from the parathyroid gland and to a method of producing same. The hormonal substance, LITORALON, has therapeutic application in the treatment of irradiation injury of mammalia.

BACKGROUND OF THE INVENTION

The literature has described hormones of the parathyroid gland, namely, parathormone having a molecular weight of 8,500, which increases the blood calcium level of the organism.

This hormone is a substance of polypeptide structure and is prepared by extracting ground and degreased parathyroid gland with warm hydrochloric acid or phenol.

OBJECTS OF THE INVENTION

It is an object of the invention to provide a new hormonal substance, also derived from the parathyroid gland, which has utility in the treatment of irradiation injury in mammals.

It is another object of the invention to provide a method of obtaining the new hormonal substance.

It is another object of the invention to provide a method of treatment of mammalian subjects for irradiation injury.

It is also an object of the invention to provide pharmaceutical and therapeutic compositions incorporating the hormonal substance.

DESCRIPTION OF THE INVENTION

The present invention is based on my surprising discovery that the parathyroid gland contains in addition to the known hormone parathormone, a further compound or compounds with hormonal effect referred to hereinafter as a hormonal substance, which differs essentially from the substance formerly described, and identified below as LITORALON.

A. General Description of LITORALON

The chemical structure of the hormonal substance LITORALON is not yet clear although extensive tests have been made to determine its character. It is also not yet clear, whether it is a compound, a group of substances, or a physical, or physicochemical allotrope of a chemical compound.

The new hormonal product can be characterized as follows:

It is soluble in water, contains C, H, N, O, S and/or P it is neither a protein nor a steroid; it is one or more micropeptide-like compounds with a molecular weight between 200–1000, it has no fatty character, it is not soluble in benzene, chloroform and carbon tetrachloride.

The hormonal product possesses the following physiological effects: it causes phosphaturia (causes the excretion of phosphates in mammalian urine), exerts a radioprotective effect (i.e. protects organisms against the detrimental effects of alpha, beta and gamma radiation), increases the adrenal cortex function (i.e. the production of corticosteroids) and also increases the trace-element (Si, Cu, Zn, Mn) concentration of the blood.

In clinical therapeutics it can be used to treat irradiation injury.

The new hormonal substance does not affect the level of calcium in the blood, unlike the known parathyroid hormone, but increase the level of silicon in the blood.

The hormonal substance has the following additional chemical characteristics: it is not precipitated with trichloroacetic acid, and is not unambigously of a protein or polypeptide character. It is soluble in water if advisable part of characterization.

While at first blush it might appear that the range of molecular weights for LITORALON (200 to 1000) might appear to exclude the possibility that the hormonal substance is a compound, it should be noted that it may be a dimer, trimer or polymer having several repeating units any one or more of which may have the active properties alluded to above or described in some detail below. Of course, this should not exclude the possibility that, if LITORALON is not a single compound or a compound characterized by the fact that it is made up of a number of repeating units, it may be two or more discrete compounds associated by less than a true chemical bond. In the latter case all or part of the activity may reside in one or more of the associated units or only in their associative form. However, because of the complexity of LITORALON and the fact that it could not be more accurately characterized to date, it has been impossible to ascribe a definitive chemical formula thereto or to further delimit the molecular weight of the hormonal substance of the present invention.

B. Method of Obtaining — General

The LITORALON hormones and concentrates or mixtures containing the same, are prepared by drying and grinding the parathyroid gland of a mammal which may previously be degreased, whereafter it is extracted with water and the solution obtained is lyophilized. Suitable starting materials for the preparation of LITORALON are also the tissue or cellular cultures derived from the parathyroid gland of mammals.

The concentrate thus prepared, in an aqueous solution, or as the lyophilized powder, exhibits the therapeutic or biological effects described.

The purer products are more convenient starting materials for pharmaceutical products for esthetic or precise dosage reasons.

The aqueous extract may be made free from proteins and polypeptides by adding to the extract an agent precipitating the proteins and using the solution obtained after elimination of the precipitating agent.

As protein precipitating agents trichloracetic acid and sulfosalicylic acid may be used. Also methods of removing the proteins by adding solvents and by salting them out can be used. The excess of trichloracetic acid can be removed by a series of extractions with ether.

According to my observations the separation of protein, polypeptide and other fractions can be also carried out with very good results by gel-filtration. In this case the desired substance can be obtained in great purity in the suitable fraction. A very practical method is the purification by gel-filtration after the elimination of proteins in the aqueous fraction. As described with gel-filtration on a column with a great separative capacity, or by a repeated gel-filtration of a small fraction, a LITORALON fraction with a relatively high purity can be obtained.

The purification of the active ingredient can be effected in several ways and for this purpose such methods as extraction, precipitation, absorption etc. and combinations thereof can be used.

As already mentioned, LITORALON has not yet been fully identified. It has been found that, with different chemical and physicochemical operations, different active LITORALON fractions may be separated from each other. Thus different fractions can be obtained by precipitation with solvents, chromatography, gel-filtration, dialysis, extraction, fractional salting out and treatment with ion exchangers. For a more differentiated separation of the fractions a combination of these methods can be employed.

Because such further separation of components of LITORALON can be carried out that does not exclude the possibility that the hormonal substance is a single compound for the reasons already noted. For example, if LITORALON is an associative compound of two or more units readily dissociated by the chemical or physicochemical operations mentioned above, the individual units will be found in different fractions, each with possible distinct activity. This applies even where the hormonal substance is a polymer and the fractions separated, for example, are the monomer, dimer, trimer etc.

C. Method of Administration — General

The present invention also relates to therapeutic and/or preventive compositions which contain as active ingredient LITORALON or fractions of LITORALON in admixture with inert, solid or liquid carriers. The active ingredient content of these compositions can vary within wide ranges and is preferably about 0.05–10 mg/dose in human therapy.

These products can be prepared by conventional methods used in the pharmaceutical industry from solid or liquid concentrates containing LITORALON, or from mixtures, in the form of tablets, suppositories, solutions, ointments, powder mixtures or sprays.

Tablets with an active ingredient content of 0.05–5 mg (product of Example III) can be prepared by a wet granulation process, although dry technology is also applicable. Any kind of harmless, inert additives which have hitherto been employed in the pharmaceutical industry can be used to make tablets.

An injectable solution may be prepared from an aqueous solution in a concentration of about 0.05–5 mg/ml, but in this case the above mentioned removal of proteins is necessary and the perfect removal of the protein-precipitating agents is also required. The more feasible preparation of an injection solution is by the sterile filtration of the aqueous concentrate. The injection solution has no tissue irritating effect and does not cause any anaphylactic side effects.

Ointments can be prepared from LITORALON having an active ingredient content of 0.01–0.1 mg/g. For this purpose most of the basic hydrophilic and hydrophobic therapeutic ointment materials are suitable. The situation is similar in preparation of suppositories in which cacao butter and the basic synethtic suppository bases e.g. (Witepsol mass) are suitable. The active ingredient (LITORALON) content of the suppositories depends on the purity of the concentrate and should be about 0.05–5 mg.

The present invention is directed also to cosmetic preparations containing LITORALON as an active ingredient. The cosmetic preparations can be prepared from solid or liquid LITORALON concentrates with known solvents after addition of additive-, filling-, diluting-, lubricant- and carrier substances in the form of ointments, solutions, creams, emulsions, powder mixtures, sprays, etc. with a LITORALON concentration of about 0.01–0.5 mg/g.

D. Physiological Effect — General

A wide range of clinical-therapeutical investigations have been carried out with LITORALON as further described in detail. The daily dosage was three fold 0.1–0.5 mg of the LITORALON concentrate orally. Practically no harmful side effect was observed on a patient sample of about 3000 persons. In some cases the appearance of an urticarous eruption on the skin surface was observed, or, from time to time, nausea and a vomiting sensation. These complaints occured only with 5% of the treated patients and were not considered significant in light of the therapeutic effects achieved.

The following physiological effects are characteristic of the hormonal substance according to the invention.

a. Pharmacological effect of administration of LITORALON

The calcium level in the blood serum is not practically affected. There is an increase of the blood silicon content and modification of the concentration of other essential trace elements, e.g. Zn, Cu, F.

Produces phosphaturia and increases the organic monophosphate and cyclic monophosphate level (cAMP) in the urine.

Decreases the blood sugar content.

Affects the blood coagulation.

Increases lipolysis.

It protects against the harmful effect of electromagnetic radiation. It decreases the regression time of skin erythema and significantly increases the survival of rats irradiated with a lethal ray dosage and protects against bone marrow injury induced by irradiation. It moderates the antimitotic effect of bone-marrow myelocytes induced by ray radiation.

It has been found to exert not only a prophylactic, but also a therapeutic effect against radiation injury.

b. Clinical effect of administration of LITORALON

The hormonal (LITORALON) has been found to be effective in the treatment of human patients for irradiation injury.

The pharmacological and chemical tests have been regularly carried out for several years by eight university chairs, national institutes and pharmaceutical factories. The clinical tests were carried out by 20 university clinics, national institutes and hospitals in Budapest over the same period. The therapeutic tests on different clinical indications have reached 3000 persons. The therapeutic effect on some clinical indications appears only after a regular treatment of several weeks or some months.

The pure fractions display their therapeutic effect in a very small concentration (in a concentration of 1/1000 ppm, or below, corresponding to an oral dose of one microgram/kg body weight).

The fact that LITORALON significantly influences the silicon content of the blood and has a decisive role in silicon-level regulation (in 30 days on rats and rabbits the treatment with LITORALON results an increase of the blood-silicon content by more than 100%), emphasises the very important physiological role of silicon in the glyco-mucoproteid synthese and in the management of its physiological functions (similarly to the sulphate ion).

It seems likely, that the hormones with LITORALON character are produced in the so-called eosinophil cells of the parathyroid gland.

SPECIFIC EXAMPLES

EXAMPLE I 10 g of lyophilized and ground parathyroid gland powder derived from cadavers or such slaughterhouse animals as cows, pigs, horses, sheep are degreased in a known manner (Aurbach) as follows.

The gland powder is mixed at room temperature with 25 ml of abs. acetone and then filtered on a glass filter No.$G_4$. The well drained gland powder is again mixed at room temperature with 25 ml of chloroform and filtered on a glass filter No. $G_4$; this operation is repeated. The filtered substance is suspended again in 25 ml of abs. acetone, and sucked on a glass filter No. $G_4$. The obtained gland powder is dried in vacuo at room temperature. The weight of the dry substance obtained varies from 7-9 g, depending on the fat content of the initial substance.

10 g of degreased dry gland powder are extracted with three-fold 100 ml of distilled water at room temperature for 1 hour under a nitrogen atmosphere. Between the extractions the gland powder is separated from the liquid phase by a high speed laboratory centrifuge. The extracted fractions are stored at a temperature of 3°–5° C, in a nitrogen atmosphere until used further. The aqueous extracts are ninhydrin, biuret and trichloro-acetic acid positive.

Thereafter the aqueous extracts are collected and an amount of a 50% volume % trichloro-acetic acid is added with constant dropping rate and shaking to a final trichloro-acetic acid concentration should be 15%.

After standing for 1 hour at a temperature of 3°–5° C the trichloro-acetic acid precipitate is centrifuged. The upper layer is a clear aqueous solution, which trichloro-acetic acid negative, and ninhydrine positive.

The excess of trichloro-acetic acid is removed by serial extractions at room temperature with an aqueous solution of ether (1–1.2 vol. ether: 1 vol. water). For the total removal of the trichloro-acetic acid generally 17–18 extractions are necessary; in practice 20–25 extractions are carried out.

After the last extraction the pH of the aqueous phase must have a value of 4.5–5.

The removal of ether lasts 6 hours and is carried out in a nitrogen atmosphere, by means of a water pump at a temperature not exceeding 30° C.

The removal of ether is connected with a decrease of the volume (one part of the aqueous phase is distilled off too).

The total removal of ether is ascertained by smelling.

The aqueous solution is thereafter lyophilized and stored in a well closed vessel (it is hygroscopic).

The yield related to the total amount of initial gland powder (before degreasing) is 10–15%, depending on the fat content.

The lyophilizate of the protein-free aqueous solution contains one unit per milligram (U/mg) of the active principle. The biological determination of the standard unit (U) of LITORALON is given below.

EXAMPLE II

Applying the method described in Example I, an extract from the protein content and of the precipitating agent is prepared from an aqueous extract of degreased parathyroid glands. 5 g of a trichloro-acetic acid inactive liophilizate are gel-filtered on a column containing Sephadex $G_{15}$ (Dextran Polymer, diethylaminoethyl). Size of the column is 4.3 fold 144 cm. The eluent is water.
Flow speed: 60 ml/hour.
Size of fraction: 15 ml.
Weight of the collected lyophilized samples during fractionation:

| Number of tubes | Weight/mg |
|---|---|
| 46 – 83 | 913 |
| 84 – 98 | 1126 |
| 99 – 118 | 999 |
| 119 – 136 | 1416 |
| 137 – 154 | 24 |
| 155 – 170 | 3 |
| 185 – 198 | 19 |
| 221 – 230 | 2 |
| 238 – 265 | 15 |
| 279 – 285 | 1 |
| TOTAL | 4518    mg /90 %/ |

The main fraction tube number 46–83, containing 913 mg is rich in LITORALON and possesses in an oral dose of 5–10 micrograms/kg body weight an express physiological, and therapeutical activity.

This is the substance containing the first two peaks of the gel-filtration.

The suitable separation of the fraction can be carried out with the following methods of detection.
 a. Measuring spectrophotometric absorption at 280 millimicrons.
 b. Measuring spectrophotometric absorption at 234 millimicrons.
 c. Measuring spectrophotometric absorption at 360 millimicrons.
 d. Measuring electric conductivity.
 e. A qualitative analysis of chloride ions with silver nitrate.
 f. The pH measuring of the fractions belonging to the different peaks.
 g. Investigation with ninhydrin reagent.
 h. Investigation with the naked eye of the opalescence and color yellowish.

The yield of the main fraction 46–83 is 2–2.5% calculated on the dry, not degreased parathyroid powder.

The lyophilizate of the protein-free aqueous solution contains 10 units per milligram (U/mg) of the active principle. The biological determination of the standard unit (U) of LITORALON is given below.

EXAMPLE III

The process according Example 2 is carried out except, that the two first peaks are collected in separate main fractions. Thus 302 mg main fraction I, and 555 mg of main fraction II are obtained from 5 g of a protein free aqueous extract.

Thereafter the main fraction II is gel-filtered again. 456 mg of the substance are carried on the column, water is used as an eluent. The size of the column 4.3 fold is 144 cm; the flowing speed is 50 ml/h. The size of the fraction is 10 ml.

Filler: Sephadex $G_{15}$.

Thus the II. main fraction can be split into three further peaks. The fractions belonging to the middle peak are united. The weight after lyophilizing is 237.5 mg.

The yield calculated on a dry, not degreased parathyroid gland powder is 0.6–0.8%.

The lyophilizate of the protein-free aqueous solution contains 10U/mg of the active principle.

Characteristics properties: a yellow colored hygroscopic substance which contains C,H,N,O, S, and/or P. Characteristic groups are: —SH, —COOH, —OH. According to a mass spectrographic analysis the following characteristic fragments were found: $C_7H_{11}N_5O_2S$, $C_5H_9N_5O$, and $C_4H_6NO$.

It can be supposed, that one of the molecules is a purine (guanine) derivative with a side chain containing a sulfhydryl group.

The fraction contains other structures too. (E.G. amino acids as impurities. This fraction has a definite physiological and therapeutical effect even in a dose of 1 microgram/kg body weight.

The product can be purified by chromatographic and other methods.

By means of a column filled with cellulose or an ion-exchange resin the contaminating amino-acids can be removed (lysine, glutaminic acid, glycine). Thus LITORALON can be obtained, still contaminated, with a yield of 0.3–0.4% calculated on the dry parathyroid gland powder. This product is effective in a concentration below 1 mcg/body weight kg.

EXAMPLE IV

The substance described in Example I is gelfiltered on Sephadex G-15 ("Pharmacia" made in Sweden, particle size 90–120 microns) with descending technology.

The elution diagram is measured at 280 nm extinction. Measuring the volume of the liquid quantity coursed down by the function of the extinction, the second peak from the beginning contains the LITORALON.

The characteristic parameters of gelfiltration are as follows.

Measurement: 5.1 g substance (from Example 1.) dissolved in 10 ml of water.
Diameter of column: 4.85 cm
Height of column: 149 cm
Flowing velocity: 0.78 ml/minute
Time: 10 minutes Fraction size: 7.8 ml/tube

| | |
|---|---|
| A peak | 77–103 tubes |
| B " | 104–128 " |
| C " | 129–134 " |
| D " | 135–162 " |
| E " | 163–189 " |
| F " | 190–217 " |
| G " | 218–227 " |

The peak B contains the active ingredient.

Elution volume of 104 tubes is 814 ml. The whole volume of peak B is 188 ml.

Between the peaks D and E the chlorine reaction is positive. The dry lyophilized weight of peak B varies between 0.43–0.53 g in case of about 5 g starting material.

The lyophilizate of the protein-free aqueous solution contains 10U/mg.

Identification by gelfiltration:

After gelfiltration on Sephadex G-15 the substance has to appear in the eluate at $(0.67 \pm 0.02) \times V_o$ if detected by absorption at 280 μm in aqueous solution. $V_o$ is the volume at which the salt appears in the eluate. (Positive chlorine reaction.) The peak B is fractionated on a Dowex 50×2 column at pH 1.8.

301 mg substance in 30% aqueous solution is applied on a Dowex 50×2 column of 132×1 cm, which previously was equilibrated with a mixture of formic acid-acetic acid to pH 1.8. Flowing velocity: 13 ml/hour. Size of fraction: 4 ml. The fractions are detected at 280 μm. 9 elution peaks are obtained:

| Sign | Tubes | Weight (mg) |
|---|---|---|
| A | 9–12 | 8.4 |
| B | 13–17 | 18.4 |
| C | 18–23 | 64.4 |
| D | 24–29 | 5.2 |
| E | 30–36 | 2.2 |
| F | 37–42 | 0.5 |
| G | 43–50 | 3.1 |
| H | 51–57 | 7.3 |
| I | 58–80 | 6.8 |
| | | 116.3 (38.6%) |

The active ingredient can be detected in fractions D, E and F.

The fractions mentioned before are applied to Whatman 3 MM 22 cm broad filter paper and electrophoretized at pH 1.8 and 1500 V for 90 minutes:

The active ingredient is ninhydrin positive and migrates uniformly from the starting line towards the positive pole 5 cm/90 min. at 1500 V.

The product isolated by means of electrophoresis is eluted with water and his biological activity is tested. Yield of the isolated product is 0.01–0.02% calculated on the dry gland powder.

The LITORALON obtained by this way may be considered chemically almost pure and its biological activity was proved by the following tests:

The serum phosphate concentration of rats was significantly decreased by a dosage of 3 gamma/120 g. In the same dosage it decreased significantly the blood sugar. (Dosage: s.c.)

EXAMPLE V

After carrying out the process described in Example I the lyophilized endproduct is subjected to a dialysis. After dissolving 700 mg of the substance in 33 ml of distilled water it is dialyzed in a dialysis-membrane (Kalle 44). Dialysis is carried out against 2fold 100, and 13fold 150 ml of distilled water, so that the outer aqueous phase is completely changed in 3.5 hours; in the three nights the aqueous phase must be changed in all 16–16 hours. The dialysis is carried out at a temperature of 5° C.

In the membrane 41 ml of the solution are retained (undialyzed part).

The lyophilized product contains 35 mg of a dried substance.

On evaporating the outer phase at 30° C in vacuo and lyophilizing 662 mg of a dried substance are obtained.

EXAMPLE VI

Proceeding as described in Example I and starting from 20 g of gland powder (lyophilized and not degreased) the aqueous solution freed from protein and ether is evaporated in vacuo to one-third of its volume, whereupon it is admixed three times with a 1 : 1 (volume) of chloroform. The aqueous layer is freed from chloroform under nitrogen in vacuo. The chloroform-free aqueous solution is further evaporated in vacuo to a volume of 20 ml and a five-fold amount of acetone is added. The solution is allowed to stand on ice overnight. From the nearly colorless acetonic phase a yellow colored oily part is separated. The acetonic solution is decanted and the yellow oily substance is dried in vacuo until its weight is constant. 1.1 g of a resinous concentrate is obtained (A).

The decanted acetonic solution is evaporated to dryness in vacuo. 1 g of a resinous concentrate is obtained (B).

EXAMPLE VII 50 g of a lyophilized gland powder are degreased as described in Example I. 38 g of a degreased gland powder are obtained which are admixed with 400 ml of a 10% urea solution, after standing for 1 hour it is added to 400 ml of glacial acetic acid and 400 ml of acetone. The mixture is allowed to stand for 1 hour and then a further amount of 1200 ml of acetone and 11.2 ml of a N sodium hydroxide solution are added, it is allowed to precipitate, and filtered through a layer of gauze. 2 lit. of ether are added to the aqueous, urea containing acetonic solution, which is then allowed to stand overnight and decanted. The suspension is centrifuged, twice washed with 50 ml of a 1 : 1 acetone-ether mixture each. The precipitate obtained is admixed with 200 ml of a 10% acetic acid solution and dissolved. From the solution a precipitate is obtained by adding 10 g of sodium chloride. The precipitate is dissolved in 50 ml of water. It is dialysed 6 times with 2 liters of water each, the exhausted dialyzing water is decanted and the residue lyophilized. 732 g of a solid concentrate are obtained (substance C). The substance retained in the solution (197 ml) after precipitating with sodium chloride and centrifuging is treated with 40 ml of 45% trichloro-acetic acid and centrifuged. The upper layer is then dialyzed 4 times with 3 lit. of water each, evaporated in vacuo and lyophilized. 86 g of a concentrate are obtained (substance D).

7. BIOLOGICAL DETERMINATION OF LITORALON

A. Radiation protecting effect of LITORALON

1. METHOD:

Super Lilliput (Medicor, Budapest) X-ray apparatus of 180 kV tube voltage was used. Non-narcotized animals were irradiated by 7.8 R/min dose-output, at 4 mA, through a filter of 0.5 mmCu, at 50 cm focal distance. The male CFE rats (bodyweights ranging from 150 to 250 g) kept in separate plastic cages received X-ray in a dose of 850 R.

Under the effect of LITORALON concentrations the survival time of irradiated rats is increased.

Rats were covered by a buckler made of lead, and to the skin of their back, to a circle-shaped field of 1 cm radius 700 + 500 + 500, i. e. total 1700 R were given, in three parts.

Under the effect of LITORALON significant reduction in irradiation hyperaemia is noted and earlier pigmentation can be experienced.

2. EXPERIMENTAL POPULATION:

Three groups of 10 rats were used to examine both the survival times and the reduction of X-ray induced erythema.

First group: Control. Animals are exposed to irradiation as described earlier. Two days prior to and two days following irradiation they are given i. p. 1 ml physiological saline, daily.

Second group: The experimental animals receive the same X-ray dose, but instead of physiological saline they are given the LITORALON concentrate of unknown quantity, dissolved in 1 ml of water. Administration is also intraperitoneal. Injections are given on the day of irradiation and through-out the 3 successive days.

Third group: X-ray dose is the same as in the first group but, instead of physiological saline the animals are injected for 4 days before irradiation 1 ml aqueous solution of 0.1 mg AET (2-amino-ethylisothyuronium-bromide-hydrobromide), daily. Administration is intraperitoneal.

Survival time is determined during a 21 day period of observation. The times of death are fixed within the 21 day interval.

The determination of skin erythema is by means of one week observation. The appearance of hyperaemia, its intensity, and the beginning of pigmentation are registered.

3. EVALUATION:

One unit of LITORALON is that amount of the active agent which, by using the described experimental method and set up effectuates a 50% (mean value) increase in the survival of rats until the 21st day, e.g. While in the control group the number of surviving animals is 4, in the treated group it amounts to 6.

Considering that in the above experimental set up the effect of LITORALON is the same as that of AET, one of the best known, most effective radioprotective agents, we can also say that one unit of LITORALON represents that amount of the active agent which corresponds to the effect of a 4 day pretreatment with AET, given in daily doses of 0.1 mg/rat, i.p. as described earlier.

Three days after the performance of the skinerythema test, the control group displays strong hyperameia of the irradiated area and pigmentation of medium degree occurs by the 5th day.

Animals treated with LITORALON concentrate and AET, respectively, manifest significantly milder hyperaemia, compared to the controls and the pigmentation of the skin appears already on the 3rd day. One unit of LITORALON is that amount of the concentrate which exerts the same mitigating effect on skin erythema as 0.1 mg AET administered, i.p.

4. REMARKS:

The radioprotective action of LITORALON is in good accordance with clinical findings. Erythema usually occurring in irradiated patients is significantly milder when LITORALON is administered orally; pigmentation of the skin begins sooner. Slight injuries of the mucous membrane can be prevented by LITORALON, e.g. the tormenting dessiccation of the mucosa and racking fits of cough lasting for weeks following irradiation of the neck fail to occur after pretreatment with the drug. Promising experience has been obtained in the therapy of torpid skin ulcerations occurring after irradiation with extremely high therapeutic doses.

B. Protecting effect of LITORALON against the rise in serum Ca in chronic experimental fluoride poisoning

1. METHOD:

Rabbits are treated rectally with sodiumfluoride and with the combination of sodium fluoride + LITORALON. Animals receiving only sodium fluoride develop hypochromic aneamia. Serum Ca level is high; phosphate level is low. In rabbits given a combined treatment, i.e. appropriate doses of LITORALON, no anaemia develops, serum Ca is significantly lower and phosphate level is higher that in the first group.

The simplest and most accurate way of biological titration is the determination of the antagonzing effect of LITORALON against the rise in serum Ca level evoked by chronic sodium flouride treatment.

2. EXPERIMENTAL POPULATION:

Inbred male rabbits (mean bodyweight 2.5 kg ± 10%) were treated rectally with sodium fluoride 5 times a week for a period of 20 weeks.

First group: (10 animals) was given only sodium fluoride in suppositories (cacao butter). Each suppository contained 30 mg of sodium fluoride.

Second group: (10 animals) received, beside sodium fluoride, also LITORALON, either orally or rectally. The treatment lasted for 20 weeks.

3. EVALUATION:

One unit of LITORALON is the amount of the active agent mecessary to administer daily to animals with chronic experimental fluorosis to achieve a 20% fall of the serum Ca level compared to the first group (Scattering ± 5%). Each time mean values of 10 measurements were determined. A well defined dose response relationship can be obtained at a 10–30% diminution of the elevated serum Ca level.

4. REMARKS:

Increase in serum Ca level and decrease in phosphate level in experimental fluorosis is due to the Ca-binding capacity of the fluor. The organism compensates the harmful effect fluoride-ions (Ca-binding) by increasing the level of serum Ca and concomittant lowering of that of serum phosphate. From this point of view, the organism is in the state of parathormone overproduction. The administration of the hitherto unknown other hormone of the parathyroid exerts an effect contrary to that of parathormone, in experimentally induced subchronic fluorosis. LITORALON decreases the pathologically high level of serum Ca and simultaneously increases the abnormally low phosphate level. Presumably this phenomenon is based on the regulating effect of LITORALON on trace element balance. The increased Si level protects against fluortoxicosis and promotes the excretion of fluoride ions from the organism or its chemical binding. Silicon further offers protection against calcifying effects and is an activator of the mesenchyma.

5. REFERENCES:

Carlisle, E. M., Science, 167: 279, 1970
Charnot, A., Academie et Pharmacie. Proc. Pharm. 3: 136, 1959
Charnot, A., Cohen, H. et Peres, G., Proc. Int. Physiol. Sci. Congres de Washington, 81, 1968

C. Incorporation of S-35 in chick embryos

1. METHOD:

Fifteen day old chick embryos were injected intraocularly with 0.0.5 ml sodium sulphate of 10 $\mu$C activity and 0.05 ml of LITORALON concentrates with an unknown amount of active agent.

For 24 hours following injection the eggs (containing embryos) were incubated at 37 C°. Further biological processes were arrested by deep freezing to −40° C and, crystalline lenses were removed.

The crystalline lenses were homogenized in distilled water. The aliquot part was treated with trichloroacetic acid (TCA) (0.5 N end concentration) for 10 min. at 4 C° and afterward centrifuged. Radioactivity of the homogenate, supernatant and sediment was measured.

Radioactivity measured in the homogenate represents the total S-35 incorporation in the crystalline lenses, while activity of the supernatant treated with TCA indicate the S-35 content of the so called acid soluble fraction. Radioactivity of the sediment represents that of the acid insoluble fraction.

2. EXPERIMENTAL POPULATION

For each biological titration 6 times 12 chick embryos were used.

| | | | |
|---|---|---|---|
| I. | group | - | control |
| II. | group | - | 10 mg/ml of LITORALON extract (unknown) |
| III. | group | - | 1 mg/ml of LITORALON extract (unknown) |
| IV. | group | - | 0.1 mg/ml of LITORALON extract (unknown) |
| V. | group | - | 0.01 mg/ml of LITORALON extract (unknown) |
| VI. | group | - | 0.001 mg/ml of LITORALON extract (unknown) |

In addition, each group was given intraocularly 0.15 ml aqueous solution of sodium-sulphate -S-35 in a concentration of 100 $\mu$C/ml and except the control, groups from II to VI received 0.05 ml of the solution containing the active agent.

1 LITORALON unit is that amount of the active agent which, by means of the above experimental method and set up, is able to evoke a mean increase of 25% of the sulphate content in the acid soluble fraction of the crystalline lenses. (Scattering ± 20%, compared to the grade of increase).

3. REMARKS:

The increased incorporation of acid soluble sulphate is due to the enhanced formation of sulphomucopolysaccharides.

The logarithm of LITORALON concentration has a definite ratio to the acid soluble sulphate concentration in a certain concentration range, e.g.: In case of fraction P, the sulphate content of acid soluble fraction is doubled when 100 $\mu$g of the substance injected instead of 10 $\mu$g. (Fraction P is a LITORALON concentrate obtained by the following procedure: Parathyroid gland is extracted by water, from the aqueous solution proteins are precipitated by trichloro-acaetic acid, and following gel-filtration the active fraction is freeze-dried.)

It should be mentioned that, in case of higher doses (above 200 $\mu$g) the values are decreasing again. Logarithmic values of active concentrate plotted against sulphate content of acid soluble fraction yield a curve with a maximum (at + 40%). Therefore with substances of unknown LITORALON concentration it is advisable to examine the curve in the total concentration range and, determine the point of the ascending curve, where the increase of potency is 25% (Six experimental groups.)

The determination is based on one of the fundamental features of LITORALON hormone, namely, its intervention with the regulation of glyco-mucoproteide balance.

This effect is based on the recognition that the parathyroid produces two trophormones. One of them, the parathormone transforms vitamin $D_3$ in the liver and kidney to 1.25-cholecalciferol, i.e. to active hormone, in a way well known in literature. The hitherto unknown LITORALON, however, appears to transform Vitamin $A_1$ to hormone, presumably also in the liver and kidney. In this way, the two vitamins, $D_3$ and $A_1$ having fundamental importance in aquatic life presumably were transformed to prohormones at the beginning of terrestrial life (appearance of amphibia and reptilia in the course of evolution). The transformation of both vitamins into hormones is regulated by the parathyroids.

As is known, vitamin $A_1$ regulates the synthesis of sulphomucopolysaccharides almost in the same way as LITORALON does. (Logarithmic and maximum curve correlations.)

4. REFERENCES:

See: H. F. de Luca: Parathyroid hormone as a trophic hormone for 1,25 dihydroxyvitamin $D_3$, the metabolically active form of vitamin D. In: New Engl. J. of Med. 287: 250, 1972 and the following articles dealing with sulphate incorporation of vitamin A;

Subka Rao, K., Sechadri Sastry, P., Ganguly, J.: Biochem. J. 87: 312, 1963.
Carroll, J., Spencer, B.: Biochem. J. 96: 79 P, 1963.
Fell, H. B., Mellanby, E.: J. Physiol. London. 116: 320, 1952.
Fell, H.B., Mellanby, E., Pelc, S.R.: J. Physiol. London, 134: 179, 1956.
Fell, H.B., Mellanby, E.: J. Physiol. London, 119: 470, 1953.
Fell, H.B., Mellanby, E., Pelc, S.R.: Brit. Med. J. 2: 611, 1954.
Wolf, G., Varandani, P.T.: Biochim. Biophys. Acta, 43: 501, 1960.

Other biological and pharmacological effects were also suitable for determining the biological potency and unit of LITORALON, e. g. Its effect on the regulation of trace elements is also characteristic (Si, Cu, Zn, etc.). The detection of these effects, however, is not only complicated but places great demand on instruments and facilities such as atom absorption, neutron-activation analysis. Anyhow, the increase of blood silicon (50–120% in rats and rabbits) is extremely characteristic of the effect of a 2 week treatment with LITORALON as compared to the controls.

I claim:

1. A method of making a hormonal composition distinguished from parathormone in that it has a molecular weight of between 200 and 1000 and a physiological activity different from parathormone, said composition being effective in the treatment of:

Skin radiation damage, said method comprising the steps of:
 a. degreasing ground, lyophilized, protein-containing parathyroid gland powder or powder derived from tissual or cell culture of the parathyroid gland in acetone or chloroform to produce a degreased gland powder;
 b. extracting the degreased gland powder produced in step (a) with water to form an aqueous extract containing the principle associated with said physiological activity;
 c. treating the aqueous extract formed in step (b) with trichloroacetic acid to precipitate the protein therefrom and to remove parathormone contained therein to yield an aqueous solution free from the protein and the parathormone and containing the principle associated with said physiological activity;
 d. raising the pH of the aqueous extract of step (c) to a pH of 4.0 to 4.5 to produce an aqueous extract of increased pH;
 e. purifying the aqueous extract of increased pH by gel-filtering same on a gel column eluted with water and absorption spectrometrically evaluating the eluate fractions at a wavelength of 234, 280 or 300 $\mu$m;
 f. recovering from the eluate of step (e) the fraction corresponding to $(0.67 \pm 0.02) \times V_0$ where $V_0$ is the total volume of the eluate from the appearance of sodium chloride therein as detected by determining the presence of chloride ion in the eluate; and
 g. lyophilizing the fraction recovered in step (f) to form a powder constituting said hormonal composition, said powder having therapeutic effectiveness in amounts of about 0.5 to 10 milligrams per dose.

2. A hormonal substance having a molecular weight of 200 to 1000 and characterized by Vitamin A physiological activity, the ability to limit radiation damage in mammalia when administered thereto, by the tendency to cause phosphaturia by its ability to promote the healing of wounds and its ability to increase sulfur incorporation into tissues, said hormonal substance being water-soluble and consisting of at least carbon, hydrogen, nitrogen, oxygen and sulfur, said substance being effective in the treatment of:

Skin radiation damage, said substance being made by a method which comprises the steps of:
 a. degreasing ground, lyophilized, protein-containing parathyroid gland powder or powder derived from tissual or cell culture of the parathyroid gland in acetone or chloroform to produce a degreased gland powder;
 b. extracting the degreased gland powder produced in step (a) with water to form an aqueous extract containing the principle associated with said physiological activity;
 c. treating the aqueous extract formed in step (b) whith trichloro-acetic acid to precipitate the protein therefrom and to remove parathormone contained therein to yield an aqueous solution free from the protein and the parathormone and containing the principle associated with said physiological activity;
 d. raising the pH of the aqueous extract of step (c) to a pH of 4.0 to 4.5 to produce an aqueous extract of increased pH;
 e. purifying the aqueous extract of increased pH by gel-filtering same on a gel column eluted with water and absorption spectrometrically evaluating the eluate fractions at the wavelength of 234, 280 or 300 $\mu$m;
 f. recovering from the eluate of step (e) the fraction corresponding to $(0.67 \pm 0.02) \times V_0$ where $V_0$ is the total volume of the eluate from the appearance of sodium chloride therein as detected by determining the presence of chloride ion in the eluate; and g. lyphilizing the fractiion recovered in step (f) to form a powder constituting said hormonal composition, said powder having therapeutic effectiveness in amounts of about 0.5 to 10 milligrams per dose.

3. A pharmaceutical composition for mammalian disorders which consists of a pharmaceutically acceptable excipient containing a hormonal composition distinguished from parathormone in that it has a molecular weight of between 200 and 1000 and a physiological activity different from parathormone, said composition having a therapeutic effect upon Skin radiation damage, said composition being made by a method comprising the steps of:
  a. degreasing ground, lyophilized, protein-containing parathyroid gland powder or powder derived from tissual or cell culture of the parathyroid gland in acetone or chloroform to produce a degreased gland powder;
  b. extracting the degreased gland powder produced in step (a) with water to form an aqueous extract containing the principle associated with said physiological activity;
  c. treating the aqueous extract formed in step (b) with trichloro-acetic acid to precipitate the protein therefrom and to remove parathormone contained therein to yield an aqueous solution free from the protein and the parathormone and containing the principle associated with said physiological activity;
  d. raising the pH of the aqueous extract of step (c) to a pH of 4.0 to 4.5 to produce an aqueous extract of increased pH;
  e. purifying the aqueous extract of increased pH by gel-filtering same on a gel column eluted with water and absorption spectrometrically evaluating the eluate fractions at a wavelength of 234, 280 or 300 $\mu$m;
  f. recovering from the eluate of step (e) the fraction corresponding to $(0.67 \pm 0.02) \times V_0$ where $V_0$ is the total volume of the eluate from the appearance of sodium chloride therein as detected by determining the presence of chloride ion in the eluate; and
  g. lyophilizing the fraction recovered in step (f) to form a powder constituting said hormonal composition, said powder having therapeutic effectiveness in amounts of about 0.5 to 10 milligrams per dose.

4. A method of treating:

Skin radiation damage, comprising administering to the patient a hormonal substance in a dosage of 0.5 to 10 mg for a duration sufficient to ameliorate the disorder, said hormonal substance being made by the method comprising the steps of:
  a. degreasing ground, lyophilized, protein-containing parathyroid gland powder or powder derived from tissual or cell culture of the parathyroid gland in acetone or chloroform to produce a degreased gland powder;
  b. extracting the degreased gland powder produced in step (a) with water to form an aqueous extract containing the principle associated with said physiological activity;
  c. treating the aqueous extract formed in step (b) with tricholoacetic acid to precipitate the protein therefrom and to remove parathormone contained therein to yield an aqueous solution free from the protein and the parathormone and containing the principle associated with said physiological activity;
  d. raising the pH of the aqueous extract of step (c) to a pH of 4.0 to 4.5 to produce an aqueous extract of increased pH;
  e. purifying the aqueous extract of increased pH by gel filtering same on a gel column eluted with water and absorption spectrometrically evaluating the eluate fractions at a wavelength of 234, 280 or 300 $\mu$m;
  f. recovering from the eluate of step (e) the fraction corresponding to $(0.67 \pm 0.02) \times V_0$ where $V_0$ is the total volume of the eluate from the appearance of sodium chloride therein as detected by determining the presence of chloride ion in the eluate; and
  g. lyophilizing the fraction recovered in step (f) to form a powder constituting said hormonal composition.

* * * * *